United States Patent [19]

Kloots et al.

[11] Patent Number: 4,797,736

[45] Date of Patent: Jan. 10, 1989

[54] HEAD MOUNTED ILLUMINATION AND CAMERA ASSEMBLY

[75] Inventors: Jacobus Kloots, Sturbridge; Frans G. Van Der Bel, Southbridge, both of Mass.

[73] Assignee: Luxtec Corporation, Sturbridge, Mass.

[21] Appl. No.: 92,233

[22] Filed: Sep. 2, 1987

[51] Int. Cl.[4] .......................... A61B 1/04; A61B 1/06; F21V 13/04; H04N 7/18

[52] U.S. Cl. ........................................ 358/93; 128/22; 358/229; 362/33

[58] Field of Search ................. 358/93, 108, 100, 229; 128/23, 22; 362/33

[56] References Cited

U.S. PATENT DOCUMENTS

| | | | |
|---|---|---|---|
| 4,051,534 | 9/1977 | Dukich | 358/93 |
| 4,395,731 | 7/1983 | Schoolman | 358/108 |
| 4,516,157 | 5/1985 | Campbell | 358/229 |
| 4,616,257 | 10/1986 | Kloots | 358/93 |
| 4,621,283 | 11/1986 | Feinbloom | 128/22 |

Primary Examiner—Howard W. Britton
Attorney, Agent, or Firm—Wolf, Greenfield & Sacks

[57] ABSTRACT

A head mounted apparatus for illuminating a work site, and for transmitting a visual image of the work site to a remote location for viewing on a television screen. A camera and a light source are mounted on a head band which is worn by the user. The camera lens is disposed generally between the eyes of the user to allow viewing of the same image as the user is seeing. The light source is disposed slightly above the camera, and is coupled to a remote light source by a fiber optic cable. The light source and the camera are independently pivotally mounted on a bracket, and the bracket is pivotally mounted to the head band. A series of three pivotal attachments is provided so that the elevational angle of the light source can be adjusted independently of the camera and the head band, so that the elevational angle of the camera can be adjusted independently of the light source and the head band, and so that the light source and camera can have their elevational angles adjusted together with respect to the head band.

20 Claims, 7 Drawing Sheets

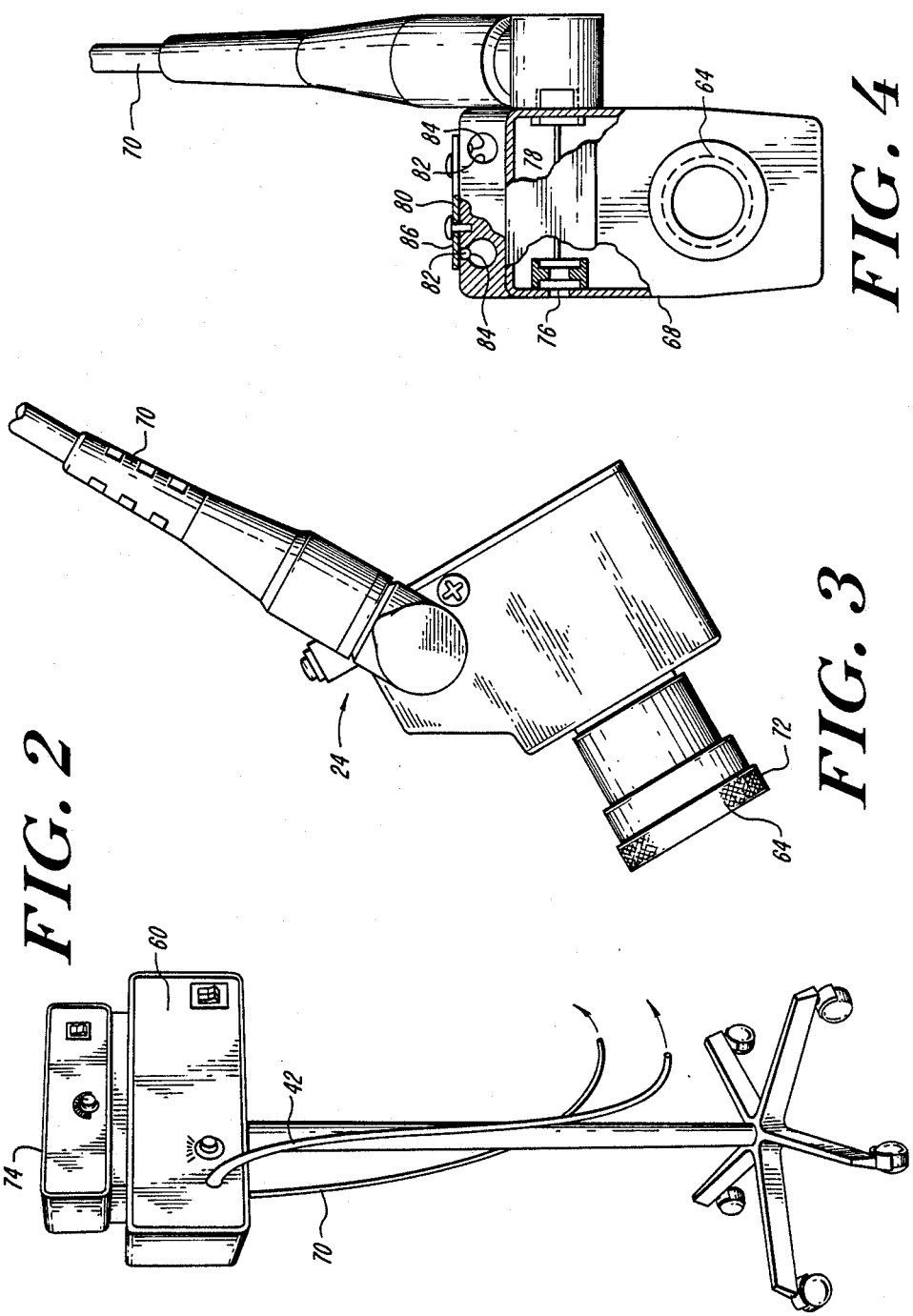

HEAD MOUNTED ILLUMINATION AND CAMERA ASSEMBLY

FIELD OF THE INVENTION

This invention relates generally to head mounted apparatus for illuminating manual operations, and more particularly, a head mounted illumination and camera assembly for permitting remote viewing of surgical operations.

BACKGROUND OF THE INVENTION

In the operating room, and in other locations where manual work is being performed by an individual on very fine objects, in deep cavities, or in hard-to reach places, often it is impossible for others to observe the operations being performed without interfering with the movements of the worker. In particular, with regard to surgeons, it is often desirable or even necessary for students or for those assisting in the operation to observe the surgery. Because most surgery is conducted in deep body cavities or in other hard-to-reach locations, it is impossible for an observer to properly view the surgery by looking over the surgeon's shoulder. In addition, these observations are best conducted at a remote location, to avoid interfering with the surgeon. One prior art solution to this problem is dolly mounted or overhead cameras, to allow remote viewing, but even these devices often cannot provide the observer with an adequate view of the operation.

Surgical operations and other fine work performed in hard to reach places require adequate illumination of the work area. This is especially true if the operation is to be viewed by others at a remote location by means of a television or other type of camera. Adequate illumination of deep cavities and the like can only be provided by a light source under the control of the surgeon.

In recent years, surgeons generally have used head mounted systems both to provide the illumination required, and to provide observers with an adequate view of the surgery. One example of such a combination illumination and camera system is found in U.S. Pat. No. 4,051,534 in which the focusing and aiming optics of the camera are remotely controlled, while the surgeon controls the location of the illumination by movement of his head. This system has certain drawbacks, because the mirrors which reflect the image into the camera lens are located on top of the surgeon's head, and do not provide an accurate view of what the surgeon is seeing. This can be a problem, especially where the operation is occurring in a deep body cavity, or in other hard-to see locations. The surgeon has no direct control over the movement of the mirrors for the television camera, and the television mirrors have limited adjustability, which restricts their permissible field of vision. The light source of this prior art device can only be adjusted by loosening and tightening a mounting screw, so that the surgeon can quickly adjust the location of the light source only by moving his head.

Another example of a head mounted illumination and viewing apparatus is that found in U.S. Pat. No. 4,616,257 assigned to the assignee of the present application. This system overcomes many of the problems found in other prior art systems such as that described above, by placing the viewing lens as well as the illumination lens between the surgeon's eyes, so that the remote viewer sees essentially what the surgeon is seeing. However, one drawback to this system is that the illumination lens and the viewing lens ar positioned one above the other and both are fixedly mounted in a single housing. Also, the center lines thereof are nearly parallel. As a result, when the surgeon is working in a position in which his face is very close to the operation site, when the light source is positioned to properly illuminate the surgical site, the viewing lens is centered on a location spaced from the site, and the remote viewer is unable to see clearly what the surgeon is doing. At best, the surgical site appears on the periphery of the area being viewed, and not in the center of the picture. Conversely, if the surgical site is centered on the viewing lens over such short distances, the site may not be adequately illuminated.

Surgical head lamps without attached television cameras also are well known, and examples are found in the following U.S. Pat. Nos. 2,651,301; 3,645,254; 3,745,993; 3,830,230; 3,951,139; 4,102,333; 4,290,422; and 4,516,190. Head mounted cameras without illumination systems also are well known, and examples are found in the following U.S. Pat. Nos. 4,395,731 and 4,516,157.

It is therefore an object of this invention to provide a head mounted illumination and camera assembly in which both the illumination source and the viewing lens can be independently and easily manipulated by the surgeon so that the surgical site can be both adequately illuminated and clearly viewed at a remote location.

It is a further object of this invention to provide a head mounted illumination and camera assembly which permits easy replacement of the viewing lens and/or illumination source.

It is another further object of this invention to provide a head mounted illumination and camera assembly in which the elevational angle of the viewing lens and the elevational angle of the illumination source are manually adjustable either independently or in unison.

SUMMARY OF THE INVENTION

In accordance with the above and other objects of this invention, a head mounted illumination and camera assembly is provided in which the camera lens and the illumination source can be manipulated easily by the surgeon either independently or in unison, and in which the viewing lens is positioned between the eyes of the surgeon to provide the remote observer with an accurate picture of what the surgeon is seeing. More particularly, both the viewing lens and the illuminating lens are pivotally mounted in closely spaced vertical relation to a bracket which is pivotally mounted to the headband. This arrangement permits independent or unitary manipulation of the elevational angles thereof so that the viewing lens and the illuminating lens can always be directed to the precise location desired by the surgeon, regardless of the distance to the surgical site.

In one embodiment of the invention, an elongated arm is provided which is pivotally mounted to the head band. The illuminating lens system is pivotally mounted at one end of the arm, while the viewing lens is pivotally attached to the arm at a point intermediate the illuminating lens and the head band mount. In another embodiment of the invention, a generally triangular shaped bracket is provided having a pivot point disposed at each of its vertices. The head band mount is pivotally attached at one pivot point, while the illumination system is pivotally attached at another pivot point, and the viewing lens is pivotally attached at the third pivot point.

Both the viewing lens and the illumination lens can be removed and replaced by other suitable systems, if desired, to provide the surgeon with a high degree of flexibility in selecting the desired type of illumination source and viewing lens. Replacement of the viewing lens is facilitated by the provision of a threadable coupling between the viewing lens and its housing. The illumination source includes a housing that is inserted into a ring, and that is held in place in the ring by an O-ring gasket which seats in a groove in the housing. Fiber optics are used in the illumination system, while the viewing lens includes an integrated circuit chip acting as a light to electrical signal transducer.

DESCRIPTION OF THE DRAWINGS

The invention will be more fully understood from the following detailed description when taken in conjunction with the accompanying drawings, in which:

FIG. 2 is a pictorial view of the remote power supply and processing circuits for the apparatus of FIG. 1;

FIG. 3 is a side view of the camera portion of the apparatus of FIG. 1;

FIG. 4 is a partially cut away front view of the camera of FIG. 3;

DETAILED DESCRIPTION OF THE INVENTION

Figure 1:
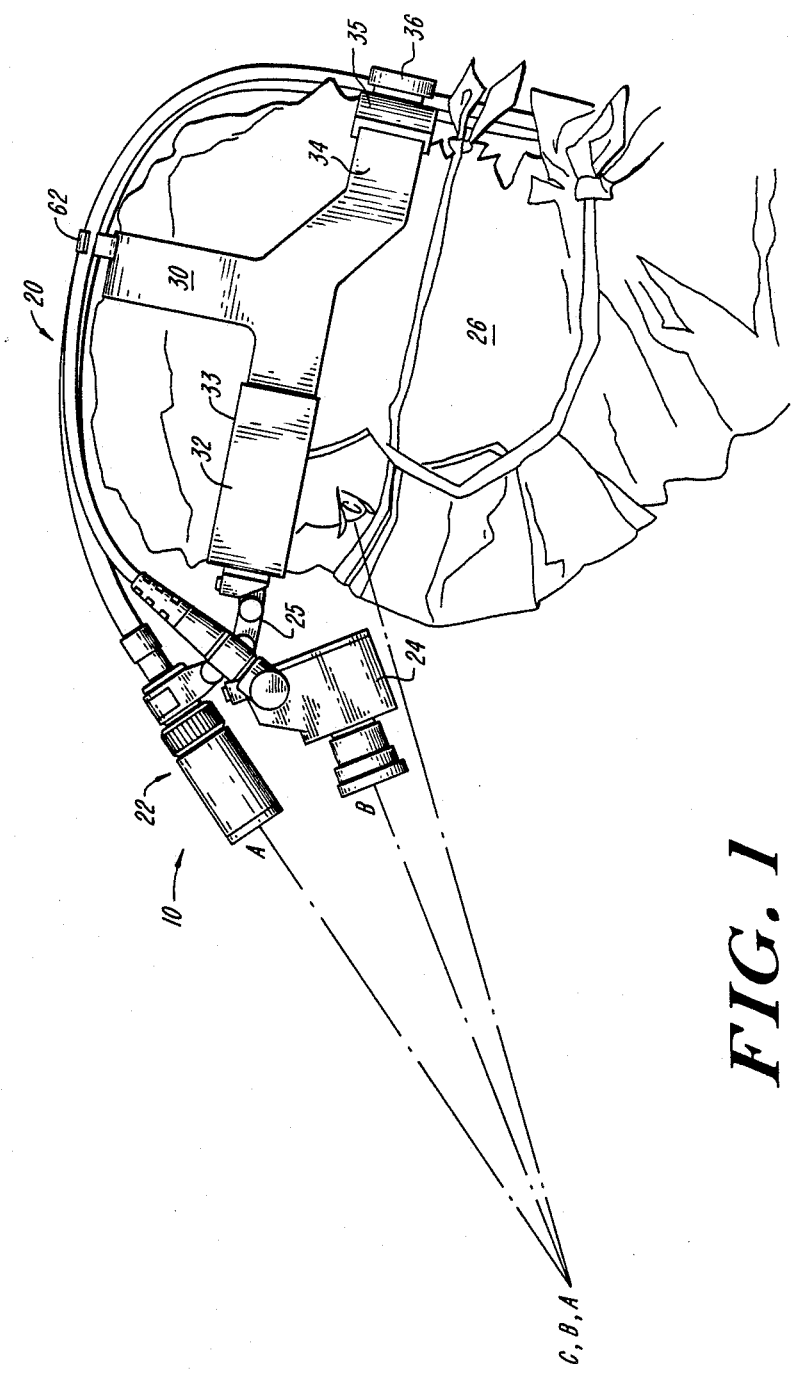
FIG. 1 is a side elevational view of one embodiment of the head mounted illumination and camera assembly of this invention mounted on a user's head.

Referring now to FIGS. 1–6, there is shown one embodiment of a head mounted camera and illumination assembly 10 of this invention. Assembly 10 includes head band 20, illumination system 22, camera 24, and bracket 25. Head band 20 is shown mounted on the head 26 of a user, such as a surgeon, whose eye are indicated by reference numeral 28. Head band 20 includes a top strap 30 which passes over the top of head 26, a front strap 32 for attachment of assemblies 22 and 24, and rear strap 34. Strap 34 includes a conventional mechanism for adjustment of the size of the head band to head 26. Strap 34 is split into two portions which fit into a hollow arcuate shaped member 35 in overlapping relation. Member 35 is provided with teeth on its interior (not shown) which are adapted to mesh with a pinion (not shown) rotated by means of exterior knob 36 to adjust the effective periphery of straps 34 and 32. Strap 32 typically has a layer of soft foam 33 or other type of padding disposed on the inner surface thereof to protect head 26. Strap 32 also contains peg 106 having groove 107 extending around the outer surface thereof for attachment of bracket 25.

Illumination system 22 includes light 38, ring 40, and fiber optic cable 42. Ring 40 is pivotally mounted onto bracket 25 by flange 41 as will be described. Cable 42 is a conventional fiber optic cable and couples light 38 to a remote light source 60 (FIG. 2) to which one end of cable 42 is attached. Cable 42 passes over the top of the surgeon's head 26 and down the back of head band 20 to light source 60 and it is held in place by snap 62 on strap 30. Cable 42 includes plug 56 which has a groove 54 extending around its outer surface.

Figure 7:
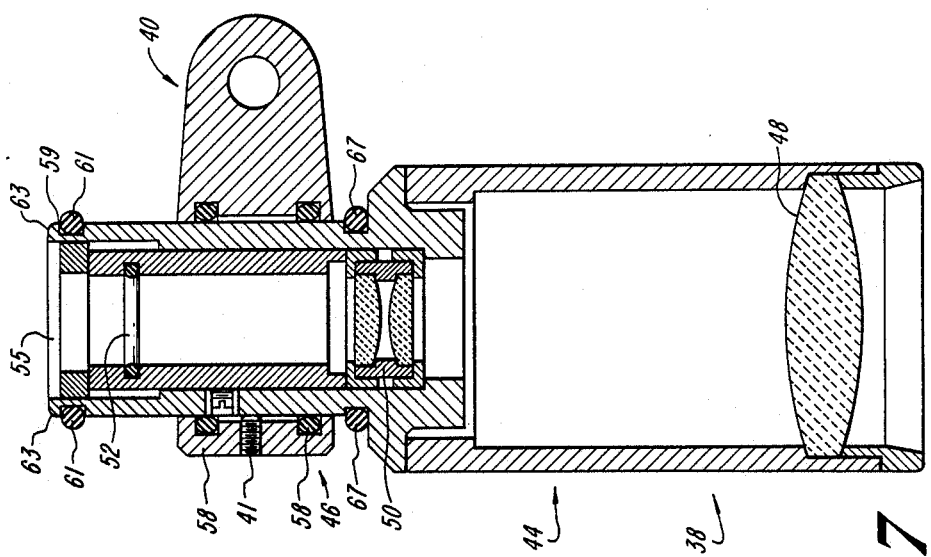
FIG. 7 is a cross sectional side view of the illumination source of FIG. 6.

Light 38 will now be described with particular reference to FIG. 7. Light 38 includes a lower housing 44 containing a lens system and an upper housing 46. Lower housing 44 of light 38 is conventional and includes a field lens 48. Upper housing 46 includes a socket 55 adapted to receive plug 56 of fiber optic cable 42 and a condenser lens assembly 50. A recessed spring 52 is disposed on the inner surface of socket 55 and is adapted to seat in groove 54 of cable plug 56 to hold the plug in place within the socket facing lens assembly 150. A groove 59 extends around the entire circumference of the outer surface of upper housing 46. An O-ring gasket 61 is urged over lip 63 of upper housing 46 to seat in groove 59 after upper housing 46 is inserted into and through ring 40, so that groove 59 is exposed on the opposite side of ring 40. Gasket 61 limits movement of light 38 in one axial direction, while gasket 67 on an outer shoulder of housing 46 limits movement of light 38 in the other axial direction with respect to ring 40. The interior surface of ring 40 includes a pair of axially spaced, recessed, parallel O-ring gaskets 58, which act as frictional bearings. Flexible gaskets 58 hold housing 46 tightly in place when it is not being intentionally moved, but allow light 38 to be replaced or removed by removal of gasket 61. Ring 40 may also include one or more set screws 41 which can be tightened.to secure upper housing 46 within ring 40 to prevent rotational or other movement thereof during use. Different lights 38 can be used depending upon the particular needs of the surgeon relating to the field of view and the strength of the light.

Figure 5:
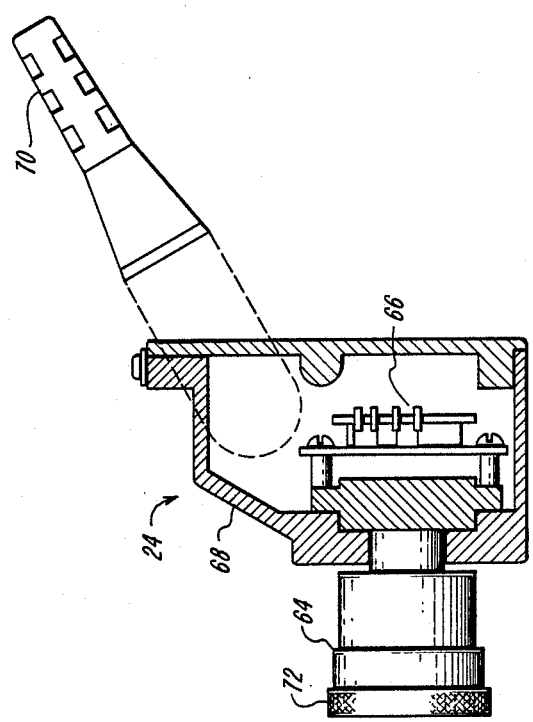
FIG. 5 is a partial cross sectional side view of the camera of FIG. 3.

Camera 24 will now be described with reference to FIGS. 3–5. Camera 24 includes a viewing lens 64, a transducer 66, housing 68, and a communications cable 70. Camera 24 is similar to that disclosed in U.S. Pat. No. 4,616,257 assigned to the assignee of the present application. Lens 64 can be either a fixed focus lens, or a variable focus lens. Lens 64 is typically threadably mounted onto housing 68 to permit easy removal or replacement. If lens 64 is a variable focus lens, a removable ring 72 is provided on the exterior surface of the housing of ens 64. Ring 72 can be removed and independently sterilized prior to use to permit the surgeon to adjust the focus of the lens during the operating procedure without fear of contamination. Transducer 66 preferably is an integrated circuit chip and is located within housing 68 behind lens 64. Transducer 66 converts visual images into electrical signals which are transmitted to conventional camera signal processing circuits 74 (FIG. 2) via cable 70 for eventual remote display on a television screen (not shown). Camera 24 may also include a microphone 76 for recording the surgeon's comments on the procedure. A cable 78 couples microphone 76 to communications cable 70 which transmits the resulting audio signal to processing circuits 74 for recording and/or broadcasting thereof to the remote viewer.

Transducer 66 is a conventional light to electrical transducer, and one example is a transducer made by Sony under the product designation Type 1CX016K. Such a Sony transducer has 384 horizontal picture elements and 491 vertical picture elements with a sensing area of 8.8 millimeters by 6.6 millimeters. Its horizontal drive frequency is 7.16 MHZ and its vertical drive frequency is 15.75 KHZ. Its structure is that of an interline transfer charge couple device and the cell size is 23.0 micrometers (horizontal) by 13.4 micrometers (vertical). Another preferred example is a transducer made by Panasonic under the product designation MN3734F. This transducer has 422 horizontal picture elements and 489 vertical picture elements with a sensing area of 6.41 millimeters in the horizontal direction by 4.89 millimeters in the vertical direction. Its horizontal drive frequency is 10.8 MHZ, and its vertical drive frequency is 15.75 KHZ. The cell size is 10 micrometers (vertical) by 15.2 micrometers (horizontal).

Bracket 25 will now be described with particular reference to FIG. 6. As can be seen, bracket 25 is an elongated arm and is formed of segments 94 and 98 which are pivotally connected at one end of segment 98 at pivot 100. Ring 40 is pivotally coupled to bracket 25 at an opposite end of segmet 98 at pivot 104. Finger 88 for mounting of camera 24 is pivotally secured to bracket 25 by flange 89 at a pivot 102 intermediate pivots 100 and 104. Segment 94 is formed of two arms 94a and 94b which are typically generally orthogonal to one another. Arm 94b mounts bracket 25 to head band 20 and includes an aperture 108 having a spring biased ball 110 which is adapted to accept peg 106 of strap 32. Ball 110 is adapted to seat in groove 107 to provide a removable, snap fit between peg 106 and bracket 25.

Figure 6:
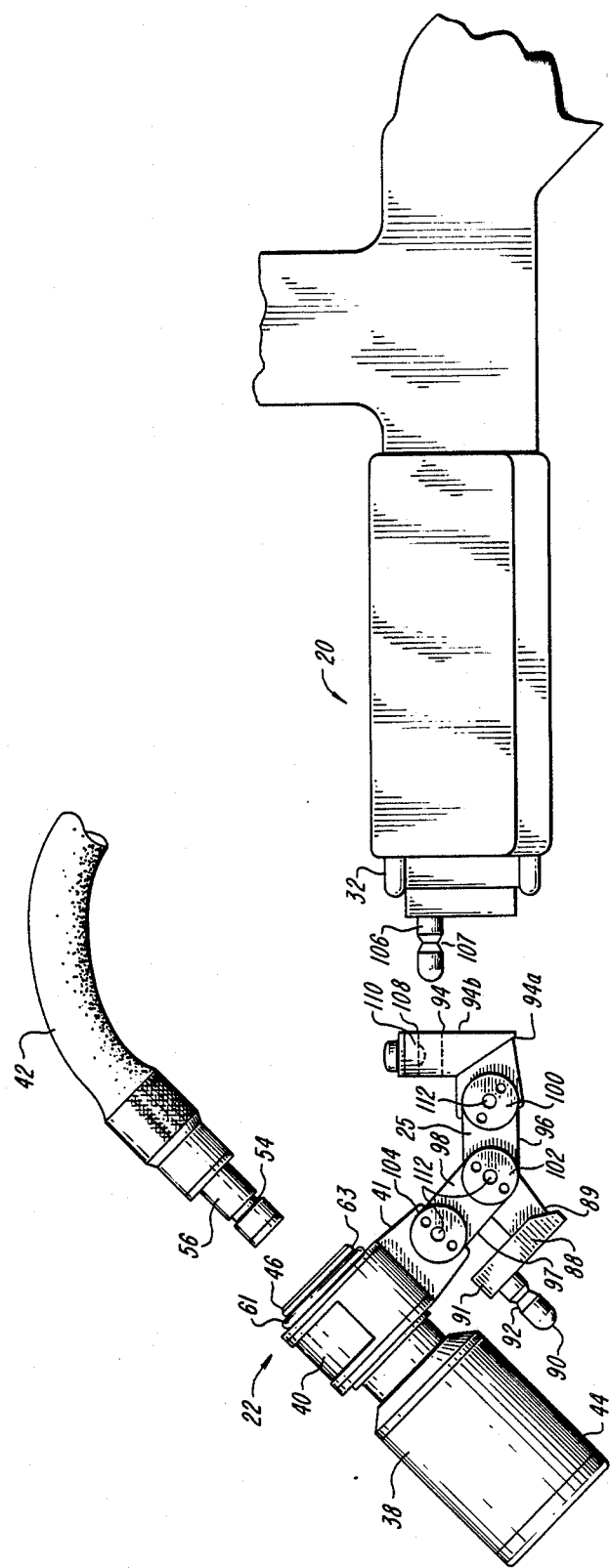
FIG. 6 is a partially exploded, side view of the illumination source, bracket and head band of the apparatus of FIG. 1.

Segment 98 is elongated and in a preferred embodiment, as shown in FIG. 6, and is generally V-shaped with two portions 96 and 97 forming an obtuse angle with respect to one another. However, in alternative embodiments, portions 96 and 97 could extend at a right angle or an acute with respect to one another, or segment 98 could be straight.

Figure 8:
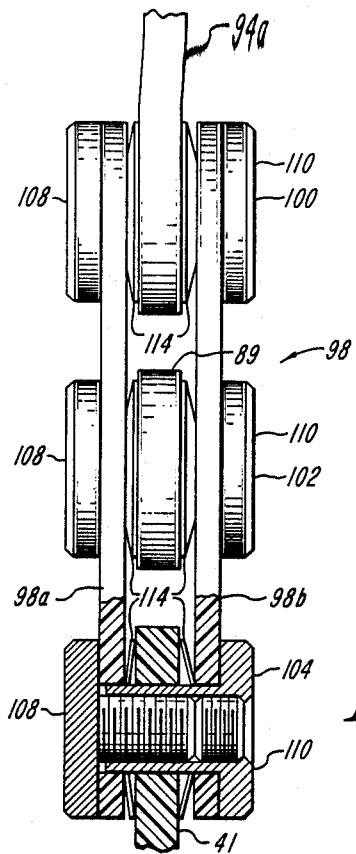
FIG. 8 is a partially cutaway, top view of the arm of the assembly of FIG. 1.

In any event, typically, segment 98 consists of two identical, spaced links 98a and 98b disposed directly opposite one another, as illustrated in FIG. 8. Arm 94a extends between links 98a and 98b at pivot 100, while flange 41 of ring 40 extends between links 98a and 98b at pivot 104. Flange 89 extends between links 98a and 98b at pivot 102, which is preferably, although not necessarily, at the juncture of portions 96 and 97.

Pivots 100, 102 and 104 can comprise any conventional pivotal connecting means which provide a friction fit so that once the segments are pivoted with respect to one another, they will remain in the desired position, until the application of a further pivoting force. Pivots 100, 102 and 104 each typically consist of two screw halves 108 and 110 which are disposed on opposite sides of each pivot adjacent links 98a and 98b respectively and which are threadably coupled together through holes in the segments 94 and 98. Screw halves 108 and 110 have enlarged heads to hold the links 98a and 98b together when screw halves 108 and 110 are threadably coupled. Screw halves 108 and 110 are locked in position with a set screw 112. Each pivot has two spaced Belleville springs 114 which are captured in place by halves 108 and 110 and which provide the desired friction at the pivot. At pivot 104, springs 114 are disposed on opposite sides of flange 41, one spring 114 between flange 41 and each of links 98a and 98b. At pivot 102, springs 114 are disposed on opposite sides of arm 94a, one spring 114 between arm 94a and each of links 98a and 98b. At pivot 102, springs 114 are disposed on opposite sides of flange 89, one spring 114 between flange 89 and each of links 98a and 98b. The amount of friction at each pivot can be decreased or increased by increasing or decreasing respectively the spacing between screw halves 108 and 110.

The manner in which camera 24 is mounted onto head band 20 will now be described with particular reference to FIGS. 1, 4 and 6. Camera 24 is provided with a mounting bracket 80 which contains two apertures 82. Each of these apertures is provided with a recessed, spring biased ball 84 which is held in place by plate 86. Plate 91 of finger 88 includes a pair of pegs 90. Each peg 90 includes a groove 92 around the outer circumference thereof. Camera 24 is mounted onto finger 88 by forcing pegs 90 through corresponding apertures 82 to urge balls 84 upwardly until they seat in respective grooves 92, thereby holding camera 24 in place. In this manner, camera 24 can be easily replaced as necessary simply by snapping it on and off pegs 90.

As shown in FIG. 4, the transverse dimension of housing 68 of camera 24 is sufficiently small that camera 24 can reside between eyes 28 of the surgeon without interfering with his vision. Preferably, lens 64 is roughly aligned with eyes 28 of the surgeon, so that the camera sees the same view as the surgeon. Preferably, line C—C representing the line of sight of eyes 28 is nearly aligned with center line B—B of lens 64. Light 38 is positioned slightly above camera 24, so that center line A—A of lens 48 forms an acute angle with respect to center lines B—B and C—C. Ideally, center line A—A of lens 48 and center lines B—B and C—C all intersect at the surgical site. The present invention permits the surgeon to maintain such an ideal relationship regardless of his position because of the articulated nature of bracket 25. The surgeon can easily manually adjust the elevational angle of the center line A—A of lens 48 of light 38 and of the center line B—B of lens 64 of camera 24 independently, or in unison. For example, light 38 and camera 24 can be adjusted in unison to maintain constant the relative angle between center lines A—A and B—B by pivoting the entire assembly only about pivot 100. If the surgeon is satisfied with the elevational angle of center line B—B of camera 24 but not with the elevational angle of center line A—A of light 38, the angle of center line A—A can be adjusted with respect to both head band 20 and the angle of camer 24 by pivoting snap ring 40 about pivot 104 independently of head band 20 and camera 24. Similarly, if the surgeon wishes to adjust the elevational angle of center line B—B of camera 24 with respect to light 38 and head band 20, finger 88 can be pivoted about pivot 102 independently of light 38 and head band 20.

Although this embodiment of the invention was described in conjunction with a preferred removable mounting of bracket 25 to head band 20, including pegs 106 and apertures 108, bracket 25 could also be fixedly mounted onto head band 20 in a known manner, such as by the use of screws or nuts and bolts (not shown).

Another embodiment of this invention will now be described with particular reference to FIGS. 9 and 10. In this embodiment, head band 20 and camera 24 are identical to those found in the embodiment of FIGS.

1-8, and they will not be described again in detail. Like numbers will be used for like parts, where possible. The primary difference between the embodiment of FIGS. 9 and 10, and that of FIGS. 1-8, is in the shape of the bracket. A different embodiment of the light is also shown for purposes of illustration, although light 38 could also be used with the embodiment of FIGS. 9 and 10, and light 150 could be used with the embodiment of FIGS. 1-8. As shown in FIG. 9, bracket 120 interconnects head band 20 with camera 24 and light 150. Bracket 120 has a generally triangular shape, with a pivot 122, 124 and 126 disposed approximately at each vertex. Segment 94 attaches bracket 120 to head band 20. Arm 94b is removably attachable to strap 32, as previously described, while arm 94a is pivotally mounted to bracket 120 at pivot 122. Camera 24 is pivotally mounted to bracket 120 at pivot 124 by bracket 128. Ring 40 is pivotally mounted to bracket 120 at pivot 126.

Pivots 122, 124, and 126 are each similar to pivots 100, 102 and 104. As shown in FIG. 10, bracket 120 comprises two identically shaped triangular plates 130 and 132. Arm 94a of segment 94, projection 127 of bracket 128, and projection 134 of ring 40 each extends between plates 130 and 132 at its respective pivot 122, 124 and 126. Arm 94a, projection 127 and projection 134 each has a hole passing therethrough. Each pivot 122, 124 and 126 includes two screw halves 136 and 138 which are threadably coupled together through the holes (not shown) in projection 134, projection 127 and arm 94a and through corresponding holes (not shown) in plates 130 and 132. Screw halves 136 and 138 are held together by set screw 140. The required friction at each pivot is supplied by two Belleville springs 142. One Belleville spring 142 is positioned at each pivot 126, 124 and 122 between projection 134, projection 127 and arm 94a respectively and plate 130, while another spring 142 is positioned at each pivot 126, 124 and 122 between projection 134, projection 127 and arm 94a respectively and plate 132. The friction at each pivot can be adjusted as required by adjusting the spacing between screw halves 136 and 138.

Figure 9:
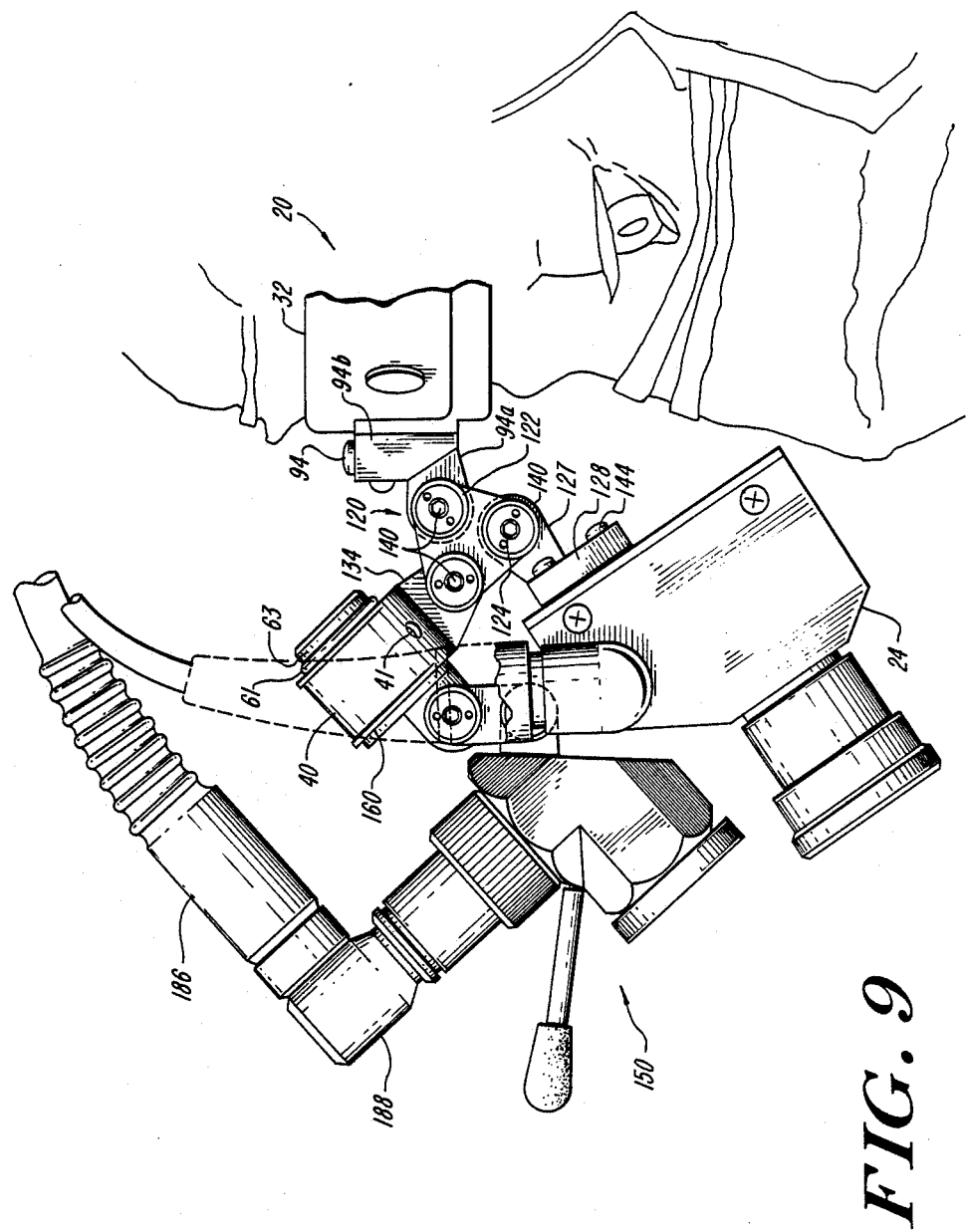
FIG. 9 is a side elevational view of an alternative embodiment of the head mounted illumination and camera assembly of this invention mounted on a user's head.
Figure 11:
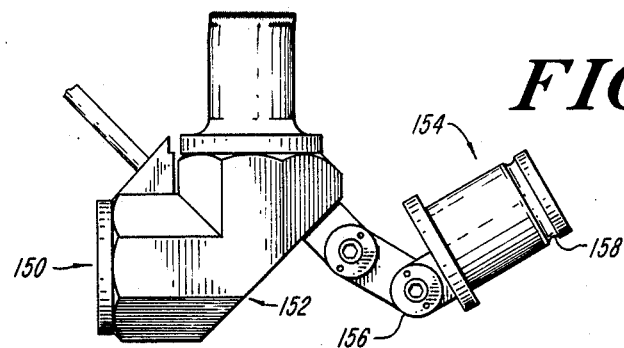
FIG. 11 is a side elevational view of the illumination source of the assembly of FIG. 9.
Figure 12:
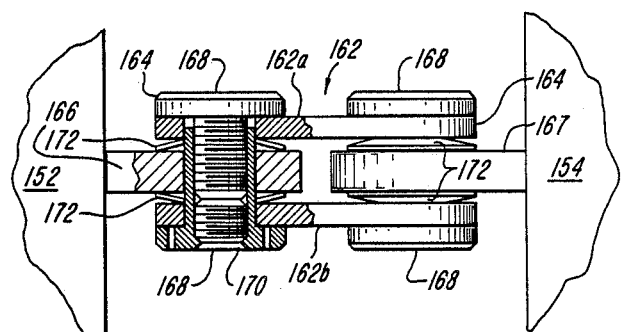
FIG. 12 is a partially cutaway bottom view of the arm of the illumination source of FIG. 11.
Figure 13:
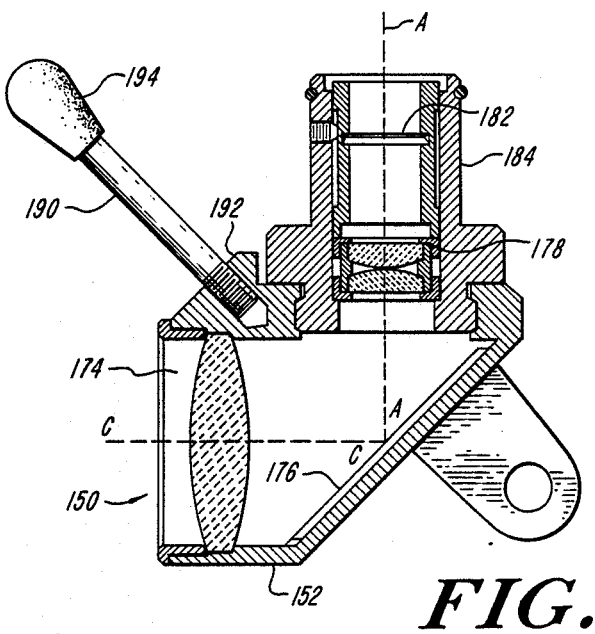
FIG. 13 is a cross-sectional side view of the illumination source of FIG. 11.

Camera 24 is shown in FIG. 9 as being fixedly mounted to elongated bracket 128 by screws 144. However, camera 24 also can be mounted onto bracket 128 using a snap fitting peg, as shown in the embodiment of FIGS. 1-8. Conversely, in the embodiment of FIGS. 1-8, camera 24 can be fixedly mounted onto finger 88, such as by screws, as shown in FIG. 9. The two methods of mounting camera 24 are interchangeable.

Figure 10:
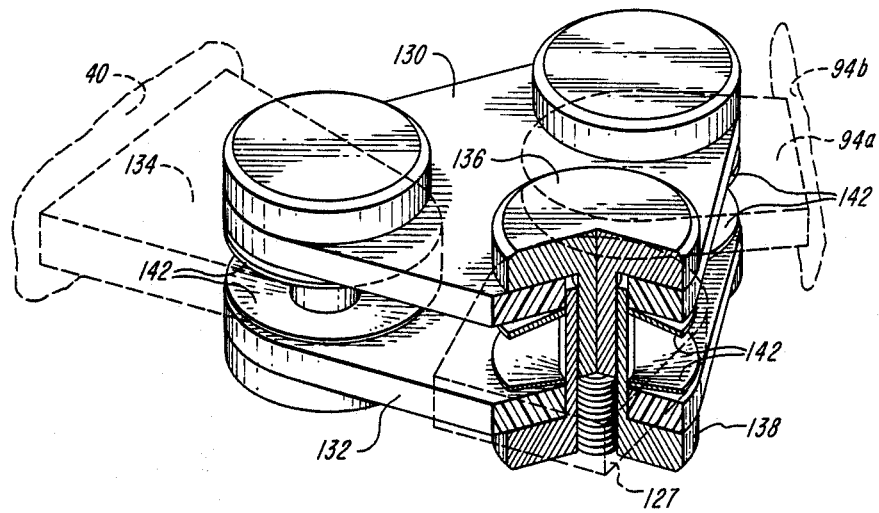
FIG. 10 is a partially cutaway, perspective view of the bracket of the assembly of FIG. 9.

In the embodiment of FIGS. 9 and 10, the center line B—B of lens 64 is very close to the line of sight C—C of eyes 28. Similarly, the center line A—A of lens 48 of light 38 is disposed at an acute angle with respect to the center line B—B of lens 64 and provides a broad illumination of the operation site. However, in the embodiment of FIGS. 9 and 10, camera 24 is positioned closer to the eye of the user than in the embodiment of FIGS. 1-8, and the angle between the center line B—B of lens 64 and the cente line A—A of lens 48 of light 38 is somewhat smaller than in the embodiment of FIGS. 1-8.

As in the embodiment of FIGS. 1-8, independent manipulation of the elevational angle of the camera and light is possible. The angular relationship between the center line A—A of the lens 48 of light 38 and the center line B—B of the lens 64 of camera 24 can be maintained while adjusting the elevational angle of both center lines A—A and B—B together by pivoting bracket 120 about pivot 122 with respect to head band 20. The elevational angle of center line B—B for the lens 64 of camera 24 can be adjusted independently of both light 38 and head band 20 by pivoting bracket 128 about pivot 124. Finally, the elevational angle of center line A—A for the lens 48 of light 38 can be adjusted independently of camera 24 and of head band 20 by pivoting ring 40 about pivot 126.

Light 150 will now be described with particular reference to FIGS. 9, 11, 12 and 13. Although light 150 is shown, for purposes of illustration, as being used only in conjunction with the embodiment of FIGS. 9 and 10, light 150 also may be used in conjunction with the embodiment of FIGS. 1-8. Conversely, light 38 can be used in conjunction with the embodiment of FIGS. 9 and 10. The two embodiments are designed to us lights 38 and 150 interchangeably.

Light 150 includes lens portion 152, mounting portion 154, and coupling 156 interconnecting portion 154 with portion 152. Portion 154 typically is hollow and is somewhat similar to upper housing 46 of FIGS. 1-8, Portion 154 includes a circumferentially extending groove 158 into which O-ring gasket 61 is snapped after portion 154 has been inserted into and through ring 40 so that groove 158 is exposed on the opposite side thereof, as previously described for housing 46. Portion 154 includes a flange 160 at the end closest to coupling 156 to limit axial travel of portion 154 into ring 40. Gasket 61 and flange 160 both limit unwanted axial movement of portion 154 with respect to ring 40, while gaskets 58 act as frictional bearings to provide a tight connection which prevents undesired movement of light 150 with respect to ring 40 during use. Set screws 41 can also be utilized to further secure portion 154 within ring 40 to prevent rotational movement thereof.

Coupling 156, as shown in FIG. 2, includes one segment 162. Segment 162 is formed of two identical, spaced links 162a and 162b. A pivot 164 is disposed at each end of segment 162 Portion 154 is pivotally connected to segment 162 at one of pivots 164 by projection 167 which extends between links 162a and 162b. Portion 152 is pivotally connected to segment 162 at the other of pivots 164 by projection 166 which extends between links 162a and 162b. The two screw halves 168 of each pivot 164 are threadably coupled together, capturing links 162a and 162b and projections 166 and 167 therebetween. A set screw 170 holds the assembly together at each pivot 164. Two Belleville springs 172 are provided at each pivot, one spring 172 being positioned between link 162a and one surface of projection 166 or projection 167, and another spring 172 being positioned between link 162b and the other surface of projection 166 or projection 167. As previously described, Belleville springs 172 provide the desired holding friction while permitting pivotal motion about each pivot 164 upon application of a pivoting force of a predetermined amount.

Lens portion 152, which is substantially identical to that shown in U.S. Pat. No. 4,516,190 assigned to the assignee of the present application, will now be described with particular reference to FIGS. 9 and 13. Lens portion 152 includes sleeve 184, fiber optic cable 186, field lens 174, reflector 176, and a condenser lens assembly 178. A recessed spring 182 disposed in sleeve 184 is adapted to snap into a recess (not shown) in right angle connector 188 of fiber optic cable 186 to hold connector 188 in aposition facing lens assembly 178.

Reflector 176 is formed of glass with a reflective coating disposed on the front surface. The optical axis C—C of lens 174 is centered on reflector 176, and the optical axis D—D of lens assembly 178 is also centered on reflector 176. Typically, the optical axis of lens assembly 178 is orthogonal to the optical axis of lens 174. Light entering through fiber optic cable 186 is focused by lens assembly 178 and is collimated into a beam which passes through field lens 174 with a predetermined spot diameter at an angle of 90 degrees from the axis of entry. If desired, an iris assembly (not shown) can be inserted to provide a variable spot diameter by changing the diameter of the illuminating beam.

A joy stick 190 may also be provided. Joy stick 190 is threadably coupled to portion 152 by means of a threaded hole 192. Joy stick 190 is removable, so that it can be sterilized or autoclaved prior to surgery, so that the surgeon may use joy stick 190 to adjust the elevational angle of center line C—C of lens 174 during surgery without fear of contamination. Joy stick 190 includes a grip 194 at its distal end. Typically, joy stick 190 is aligned substantially normal to reflector 176.

The particular arrangement of coupling 156 and the provision of joy stick 190 allows the surgeon to have further control over the elevational angle of the center line C—C of lens 174 of light 150. Light 150 can be adjusted not only to vary the elevational angle of center line C—C with respect to the center line B—B of the lens 64 of camera 24, light 150 can also be moved vertically and horizontally to change the spacing between center lines B—B and C—C, and to move light 150 toward and away from head band 20 These adjustments can be made during the course of surgery as required. Thus, if the surgeon decides, during surgery, to move his head closer to the surgical site, the light can be readily adjusted so that the center line of lens 64 and the center line of lens 174 both intersect at the surgical site. In this manner, superior illumination and full video coverage can be provided.

The operation of the apparatus of this invention will now be described with reference to all of the drawings. Initially, the surgeon may select the particular camera lens desired. If he expects to change his position with regard to the surgical site during surgery, a variable focal length lens can be selected. If the surgeon determines that his eyes will at all times be a specified distance from the surgical site, a lens with a fixed focal length can be selected that is appropriate for the circumstances. This lens can then be attached to camera 24 by use of screw threads. If the detachable embodiment is used, the camera is then snap fitted onto either bracket 25 or bracket 120 as desired. Thereafter, the appropriate light can be selected. Either the head light of FIGS. 1-8, or the light of FIGS. 9 and 11-13 can be used. Once the light has been selected, the appropriate fiber optical cable is inserted, and the light is inserted into ring 40, as described. If desired, set screws 41 are tightened. Thereafter, if removable, the whole assembly is snapped fitted onto head band 20, and head band 20 is placed over the user's head.

Once surgery has commenced, the user can adjust the focal length, if necessary, by the use of ring 72, which has been previously sterilized and snapped onto lens 64. If need be, the elevational angles of the center lines of the camera lens 64 and the light lens can be adjusted. If the embodiment of FIGS. 9 and 11-13 is used, not only can the elevational angle of the center line A—A of lens 174 be adjusted, but lens portion 152 can be moved upwardly or downwardly, toward or away from the camera, as desired.

During the course of the surgery, a surgeon can provide any comments desired through microphone 76. The electrical signals representing the visual images and the audio portion are transmitted to circuits 74 which then cause the visual images to be displayed on a remote television or CRT screen, and cause the audio to be broadcast by means of a loudspeaker or head phones. Since the center line B—B of the viewing lens 64 is close to or directly in line with the lines C—C extending from the eyes 28 of the surgeon to the surgical site, the image shown on the remote screen is virtually the same as that observed by the surgeon. When the surgeon moves his head or moves the light so that the beam falls on the area on which he s working, he is automatically causing the viewing lens to observe what he sees. The provision of a nearly coaxial line of vision for the camera lens is particularly important where the surgeon is operating in a deep or narrow body cavity. The size of the lens 64 is sufficiently small that it does not block the surgeon's view. The use of the integrated circuit chip for transmitting the visual image overcomes the weak signal with poor resolution transmitted by some prior art devices which employed fiber optics.

In view of the above description, it is likely that modifications and improvements will occur to those skilled in the art which are within the scope of this invention. The above description is intended to be exemplary only, the scope of the invention being defined by the following claims and their equivalents.

What is claimed is:

1. A head mounted apparatus for illumination and remote viewing of a work site, said apparatus comprising:
    a head band adapted to fit snugly on a human head above the eyes;
    camera means mounted on said head band for generating signals representative of the visual image received from the work site;
    means mounted on said head band for illuminating the work site; and
    means for coupling both said camera means and said illuminating means to said head band, said copling means comprising:
        a first pivot to which said camera means is pivotally secured to permit pivoting of said camera means with respect to said illuminating means and said head band;
        a second pivot to which said illuminating means is pivotally secured to permit pivoting of said illuminating means with respect to said camera means and said head band; and
        a third pivot connecting said coupling means to said head band for pivoting of said illuminating means and said camera means together with respect to said head band.

2. A head mounted apparatus as recited in claim 1 wherein said illuminating means comprises a lens coupled to a light source by a fiber optic cable.

3. A head mounted apparatus as recited in claim 1 wherein said camera means comprises a viewing lens and a light-signal to electric signal transducer located behind said viewing lens.

4. A head mounted apparatus as recited in claim 1 further comprising a microphone associated with said camera means.

5. A head mounted apparatus as recited in claim 1 wherein said camera means is positioned generally midway between eyes on the head of a user and generally on a level with a user's eyes when said head band is worn by a user, and wherein said illuminating means is disposed generally above said camera means.

6. A head mounted apparatus as recited in claim 1 further comprising a joy stick which is threadably attached to said illuminating means to permit adjustment of said illuminating means with respect to said head band.

7. A head mounted apparatus as recited in claim 1 wherein each of said pivots comprises variable friction means for preventing pivoting in the absence of the application of a force in excess of a desired amount.

8. A head mounted apparatus as recited in claim 1 wherein said coupling means comprises a generally triangularly shaped plate and wherein each of said pivots is positioned generally at a vertex of said plate.

9. A head mounted apparatus as recited in claim 1 wherein said illumination means comprises:
a first housing removably attachable to said coupling means;
a second housing, said second housing containing an illumination lens;
means associated with said second housing for accepting a fiber optic cable coupled to a remote light source;
means associated with said second housing for directing light from said fiber optic cable through said lens; and
an articulated link coupling said first housing to said second housing to permit said second housing to be pivoted with respect to said first housing.

10. A head mounted apparatus as recited in claim 1 further comprising means removably connecting said illuminating means to said coupling means.

11. A head mounted apparatus as recited in claim 10 wherein said removably connecting means comprises:
a ring pivotally attached to said coupling means at said second pivot;
a pair of spaced, flexible gaskets disposed inside said ring and extending around the inner circumference of said ring;
a housing disposed on said illuminating means adapted to fit snugly within said ring; and
a groove extending around the outside surface of said housing at an end thereof extending through said ring to be exposed on a side of said ring opposite of said illuminating means, said groove being adapted to receive a third gasket to prevent movement of said housing with respect to said ring beyond a predetermined limit.

12. A head mounted apparatus as recited in claim 1 further comprising means for removably attaching said camera means to said coupling means.

13. A head mounted apparatus as recited in claim 12 wherein said removably attaching means comprises:
a peg disposed on said coupling means, said peg having a groove extending around the outer circumference thereof;
mounting means disposed on said camera means having a hole passing therethrough; and
a spring mounted ball disposed within said hole, said ball being adapted to seat in said groove when in registration therewith to inhibit further movement of said peg with respect to said mounting means.

14. A head mounted apparatus as recited in claim 1 further comprising means for varying the focal length of said camera means.

15. A head mounted apparatus as recited in claim 14 wherein said camera means comprises:
a housing;
a lens threadably mounted to said housing; and
a removable ring snap fitted around the perimeter of said lens for grasping thereof by a user.

16. A head mounted apparatus as recited in claim 1 wherein said coupling means comprises an arm.

17. A head mounted apparatus as recited in claim 16 wherein said first pivot is disposed between said second pivot and said third pivot.

18. A head mounted apparatus as recited in claim 16 wherein said second pivot is disposed on one end of said arm spaced from said head band and said third pivot is disposed on an end of said arm adjacent said head band.

19. A head mounted apparatus for illumination and remote viewing of a hard to reach work site, said apparatus comprising:
a head band adapted to fit snugly on a human head above the eyes;
means for illuminating the work site;
camera means for generating signals representative of the visual image received from the work site; and
an arm interconnecting said head band, said illuminating means and said camera means, said arm comprising:
a first link attached to said head band;
a second link pivotally connected to said first link at a first pivot point, said illuminating means and said camera means being manually pivotable together with respect to said head band at said first pivot point;
means pivotally connecting said camera means to said second link at a second pivot point, said camera means being manually pivotable with respect to said illuminating means and said head band at said second pivot point; and
means pivotally connecting said illuminating means to said second link at a third pivot point, said illuminating means being manually pivotable with respect to said head band and said camera means at said third pivot point.

20. A head mounted apparatus for illumination and remote viewing of a work site, said apparatus comprising:
a head band adapted to fit snugly on a human head above the eyes;
means for illuminating the work site;
camera means for generating signals representative of the visual image received from the work site; and
means for interconnecting said illuminating means and said camera means and said head band, said interconnecting means comprising:
a plate;
a bracket for connecting said plate to said head band;
means pivotally connecting said bracket to said plate at a first pivot point to permit said plate, said illuminating means and said camera means to be manually pivoted together with respect to said head band;
means pivotally connecting said camera means to said plate at a second pivot point spaced from said first pivot point to permit said camera means to be manually pivoted with respect to said head band and said illuminating means; and
means pivotally connecting said illuminating means to said plate at a third pivot point spaced from said first pivot point and from said second pivot point to permit said illuminating means to be manually pivoted with respect to said head band and said camera means.

* * * * *